US007324675B2

(12) United States Patent
Raman et al.

(10) Patent No.: US 7,324,675 B2
(45) Date of Patent: Jan. 29, 2008

(54) QUANTIFICATION OF AORTOILIAC ENDOLUMINAL IRREGULARITY

(75) Inventors: Raghav Raman, Cupertino, CA (US); Sandy A. Napel, Menlo Park, CA (US); Geoffrey D. Rubin, Woodside, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 901 days.

(21) Appl. No.: 10/722,851

(22) Filed: Nov. 26, 2003

(65) Prior Publication Data

US 2004/0171932 A1 Sep. 2, 2004

Related U.S. Application Data

(60) Provisional application No. 60/429,833, filed on Nov. 27, 2002.

(51) Int. Cl.
*G06K 9/00* (2006.01)
*A61F 2/06* (2006.01)
*A61B 5/05* (2006.01)

(52) U.S. Cl. ............. 382/128; 382/131; 623/1.34; 623/1.44; 623/1.39; 623/1.46; 600/425

(58) Field of Classification Search .......... 382/128, 382/131; 623/1.44, 1.34, 1.39, 1.46; 600/425; 128/922
See application file for complete search history.

(56) References Cited

U.S. PATENT DOCUMENTS 5,755,775 A * 5/1998 Trerotola et al. ............ 606/194

| 5,881,124 | A * | 3/1999 | Giger et al. ............... 378/8 |
| 6,782,284 | B1 * | 8/2004 | Subramanyan et al. ..... 600/407 |
| 6,819,790 | B2 * | 11/2004 | Suzuki et al. ............. 382/156 |
| 2003/0204236 | A1 * | 10/2003 | Letort ..................... 623/1.11 |
| 2004/0193259 | A1 * | 9/2004 | Gabbay ................... 623/2.11 |
| 2005/0180621 | A1 * | 8/2005 | Raman et al. ............ 382/128 |

OTHER PUBLICATIONS

Prediction of Aortoiliac Stent Graft Length:Comparison of Measurement Methods, Tillich et al., stanford university school of medicine, (2000).*
Model Based Segmentation of Abdominal Aortic Aneursms in CTA images, Bruijne et al,2003 SPIE vol. 5032.*

(Continued)

*Primary Examiner*—Joseph Mancuso
*Assistant Examiner*—Nancy Bitar
(74) *Attorney, Agent, or Firm*—Lumen Intellectual Property Services, Inc.

(57) ABSTRACT

A method to quantify the radial endoluminal irregularity of aortoiliac arteries is provided. Radial endoluminal outlines of a vessel of interest are determined. The cross sectional area is determined for the area outlined by each endoluminal outline. Using this cross sectional area a shape is selected that has substantially the same area as the endoluminal outline. Subsequently, the shape is fitted to the endoluminal outline. In one aspect, the irregularity index is calculated as the ratio of the endoluminal outline and the outline of the fitted shape. In another aspect, the irregularity index is calculated as the ratio of at least a part of the endoluminal outline and the outline of the fitted shape that corresponds to the same part of the endoluminal outline. The irregularity index is visualized using a color scheme, a range of numbers, or a set of labels.

11 Claims, 8 Drawing Sheets
(3 of 8 Drawing Sheet(s) Filed in Color)

OTHER PUBLICATIONS

Compound tomography assessment of abdominal aurtic aneurysm morphology after endograft exclusion, White et al.(J Vasc Surg 2001; 33:S1-10).*

3-D deformable model for aortic aneurysm segmentation CT images ; Loncaric et al (IEEE 2000).*

Validation of Ultrasouic Image Boundary Recognition in Abdominal Aortic Aneurysm, Ravhon et al. ( IEEE 2001).*

Endograft migration one to four years after endovascular abdominal aortic aneurysm repair with the AneuRx device:A cautionary note; Coners et al;(J Vasc Surg 2002; 36:476-84).*

Tillich M. Bell RE, Paik DS, Fleischman D, Sofilos MC, Logan LJ, Rubin GD., Iliac Arterial injuries after Endovascular repair of Abdominal Aortic Aneurysms: Correlation with Iliac Curvature and Diameter. Radiology Apr. 2001;219(1):129-36.

Hatakeyama T, Shiegematsu H, Muto T. , "Risk Factors for Rupture of Abdominal Aortic Aneurysm based on Three-dimensional Study", J Vasc. Surg. Mar. 2001; 33 (3):453-6.

White RA, Donayre CE, Walot I, Woody JD, Kim NI, Kopchok GE., "Computed Tomography Assessment of Abdominal Aortic Aneurysm Morphology after Endograft Exclusion", Journal of Vascular Surgery. 2001; 33;S1-10.

Tillich M,Hill B B, Paik D S, Petz K, Napel S, Zarins C K, Rubin G D, "Prediction of Aortoiliac Stent-Graft Length: Comparison of Measurement Methods", Vascular and Interventional Radiology 2001;220:475-483.

Ravhon R. Adam D. Zelmanovitch L., "Validation of Ultrasonic Image Boundary Recognition in Abdominal Aortic Aneurysm", IEEE Trans Med Imaging Aug. 2001;20(8):751-63.

Leotta DF, Paun M, Beach KW, Kohler TR, Zierler RE, Strandness DE Jr., Measurement of Abdominal Aortic Aneurysms with Three-dimensional Ultrasound Imaging: Preliminary Report, J. Vascular Surg. Apr. 2001;33(4):700-7.

Zarins et al. (2001) in a paper entitled "The AneuRx stent graft: four-year results and worldwide experience" and published in J Vasc Surg 33:S135-145.

Holzenbein et al. (2001) in a paper entitled "Midterm durability of abdominal aortic aneurysm endograft repair: a word of caution" and published in J Vasc Surg 33:S46-54.

Makaroun et al. (2001) in a paper entitled "Is proximal aortic neck dilatation after endovascular aneurysm exclusion a cause for concern?" and published in J Vasc Surg 33:S39-45.

* cited by examiner

Figure 7

| $i$ | Proximal Neck | Distal Neck | Iliac Arteries |
|---|---|---|---|
| 1 (Normal) | | | |
| 1.01 | | | |
| 1.02 | | | |
| 1.03 | | | |
| 1.04 | | | |
| 1.05 | | | |
| 1.06 | | | |
| 1.06 | | | |
| 1.08 | | | |
| 1.09 | | | |
| 1.10 | | | |
| 1.11 | | | |
| 1.12 | | | |
| 1.13 | | | |
| 1.14 | | | |
| 1.15 | | | |
| 1.16 | | | |
| 1.17 | | | |
| 1.18 | | | |
| 1.19 | | | |
| 1.20 | | | |
| 1.21 | | | |
| 1.22 | | | |
| 1.23 | | | |
| 1.24 | | | |
| 1.25 | | | |
| 1.26 | | | |
| 1.27 | | | |
| 1.28 | | | |
| 1.29 | | | |
| 1.30 | | | |
| (Very Abnormal) | | | |

QUANTIFICATION OF AORTOILIAC ENDOLUMINAL IRREGULARITY

CROSS-REFERENCE TO RELATED APPLICATIONS

This application is cross-referenced to and claims priority from U.S. Provisional Application 60/429,833 filed Nov. 27, 2002, which is hereby incorporated by reference.

STATEMENT REGARDING FEDERALLY SPONSORED RESEARCH OR DEVELOPMENT

The present invention was supported in part by grant number 5RO1HL58915 from the National Institutes of Health (NIH). The U.S. Government has certain rights in the invention.

FIELD OF THE INVENTION

The present invention relates generally to minimal invasive surgery. More particularly, the present invention relates to a method for quantifying the irregularity of the infrarenal aorta and iliac arteries.

BACKGROUND

Treatment of abdominal aortic aneurysms (AAAs) with minimally invasive endovascular stent-grafts is gaining wide acceptance (See e.g. Zarins et al. (2001) in a paper entitled "*The AneuRx stent graft: four-year results and worldwide experience*" and published in J Vasc Surg 33:S135-145). However complications related to the breakdown of stent-graft fixation still occur (See e.g. Holzenbein et al. (2001) in a paper entitled "*Midterm durability of abdominal aortic aneurysm endograft repair: a word of caution*" and published in J Vasc Surg 33:S46-54). The characteristics of the intended proximal and distal landing zones (also referred to as attachment sites) of the stent-graft have a significant impact on its long-term stability (See e.g. Makaroun et al. (2001) in a paper entitled "*Is proximal aortic neck dilatation after endovascular aneurysm exclusion a cause for concern?*" and published in J Vasc Surg 33:S39-45). After endovascular repair, aneurysm regression leads to a progressive change in aortoiliac morphology that subjects the attachment sites of the stent-graft prosthesis to angular and torsional stress. Expansion of the proximal neck and distal migration of the device can also occur, promoting the loss of the seal between the stent-graft and the vessel wall. A breakdown of fixation can cause re-perfusion and re-pressurization of the aneurysm sac, thereby increasing the likelihood of aneurysm enlargement or rupture (See e.g. Makaroun et al. (2001) in a paper entitled "*Is proximal aortic neck dilatation after endovascular aneurysm exclusion a cause for concern?*" and published in J Vasc Surg 33:S39-45). Consequently, preoperative assessment of the intended stent-graft attachment sites is routinely performed as a part of the preoperative workup, usually by employing Computed Tomography Angiography (CTA) to quantify the size, length and angulation of the proximal and distal necks of the aneurysm and of the common iliac arteries (See e.g. White et al. (2001) in a paper entitled "*Computed tomography assessment of abdominal aortic aneurysm morphology after endograft exclusion*" and published in J Vasc Surg 33:S1-10).

However, stent-graft attachment would be compromised by excessive surface irregularity at the attachment sites. Excessive irregularity could still cause the stent-graft to have an incomplete seal, possibly causing an endoleak. The decreased contact area with the graft in the presence of a highly irregular surface could promote distal migration of the stent-graft, allowing it to slide into the aneurysm cavity. Accordingly, there is need for a method to quantify the radial endoluminal irregularity of aortoiliac arteries in preoperative CTAs.

SUMMARY OF THE INVENTION

The present invention provides a method to quantify the radial endoluminal irregularity of aortoiliac arteries in preoperative CTAs. The method could assist in preoperative planning to aid in the assessment of patients before endoluminal stent-graft surgery and could also assist in scheduling postoperative followup. The method could be incorporated into standard CT Angiography processing software packages and act as an additional aid in clinical decision-making.

Endoluminal outlines of a vessel of interest are determined using edge detection or adaptive thresholding methods in cross sectional images of a CTA. The outline should follow the flow channel of the channel and exclude calcium and a mural thrombus. The cross sectional area is determined for the area outlined by the endoluminal outline. Using this cross sectional area a shape (e.g. a circle, ellipse or a sphere) is selected that has substantially the same area as the endoluminal outline. Subsequently, the shape is fitted to the endoluminal outline using an optimization method such as e.g. a least squares method. In one aspect, the irregularity index is calculated as the ratio of the length of the endoluminal outline compared with the length of the outline of the fitted shape. In another aspect, the irregularity index is calculated as the ratio of the length of at least a part of the endoluminal outline to the length of the outline of the fitted shape that corresponds to the same part of the endoluminal outline. In still another variation, the distance of the endoluminal outline from the corresponding part of the fitted shape can be used to calculate, modify or weigh the measured irregularity. The irregularity index could be visualized or presented using a color scheme, a range of numbers, or a set of labels.

BRIEF DESCRIPTION OF THE FIGURES

The objectives and advantages of the present invention will be understood by reading the following detailed description in conjunction with the drawings listed infra. It is hereby noted that the patent or application file contains at least one drawing executed in color. Copies of this patent or patent application publication with color drawing(s) will be provided by the Office upon request and payment of the necessary fee.

FIGS. 5-7 shows examples of different visualizations or presentations of irregularity indices according to the present invention.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention is a method for characterizing the radial luminal irregularity of the infrarenal aorta and common iliac arteries as an index for assessing proximal and distal stent-graft fixation sites prior to endoluminal repair of an aneurysm. The proximal stent-graft fixation site is, for an infrarenal aneurysm, the interior surface of the aorta between the inferior renal artery and the proximal neck of the aneurysm. The distal fixation site is usually the distal interior surface of the common iliac artery. Even though the present invention is described with respect to an exemplary embodiment related to the infrarenal aorta and common iliac arteries, the present method could also be useful in characterizing a radial luminal irregularity index of any other (normal and diseased) vessel for evaluative or diagnostic purposes.

Figure 1:
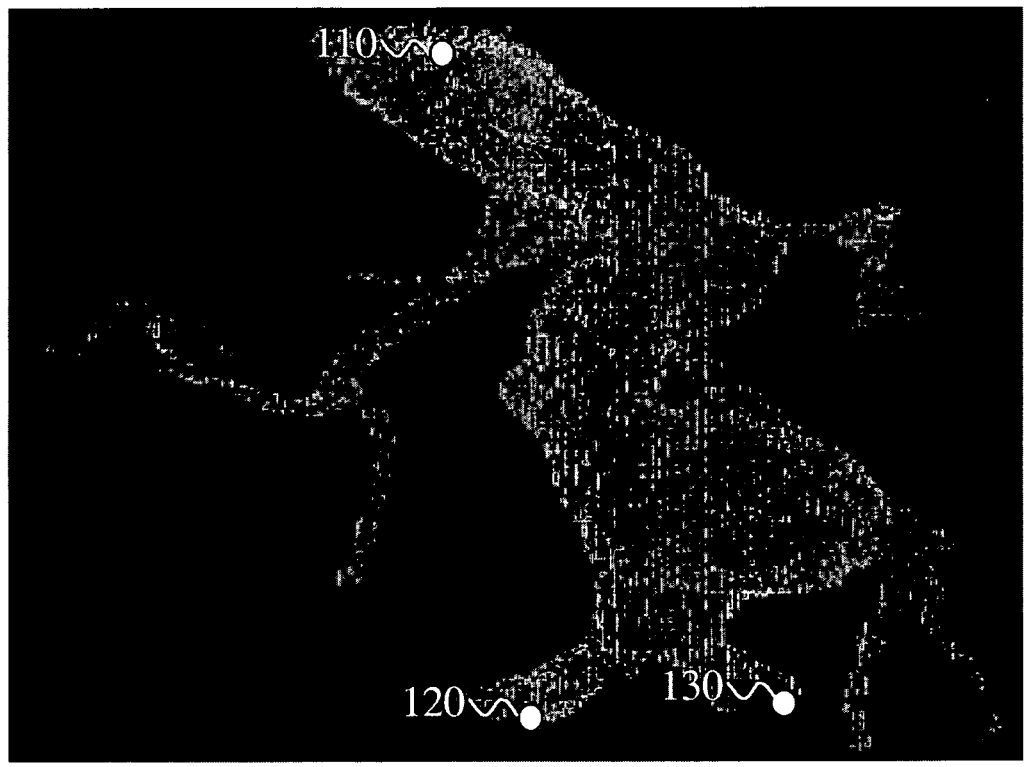
FIG. 1 shows an example of a CTA according to the present invention.
Figure 2:
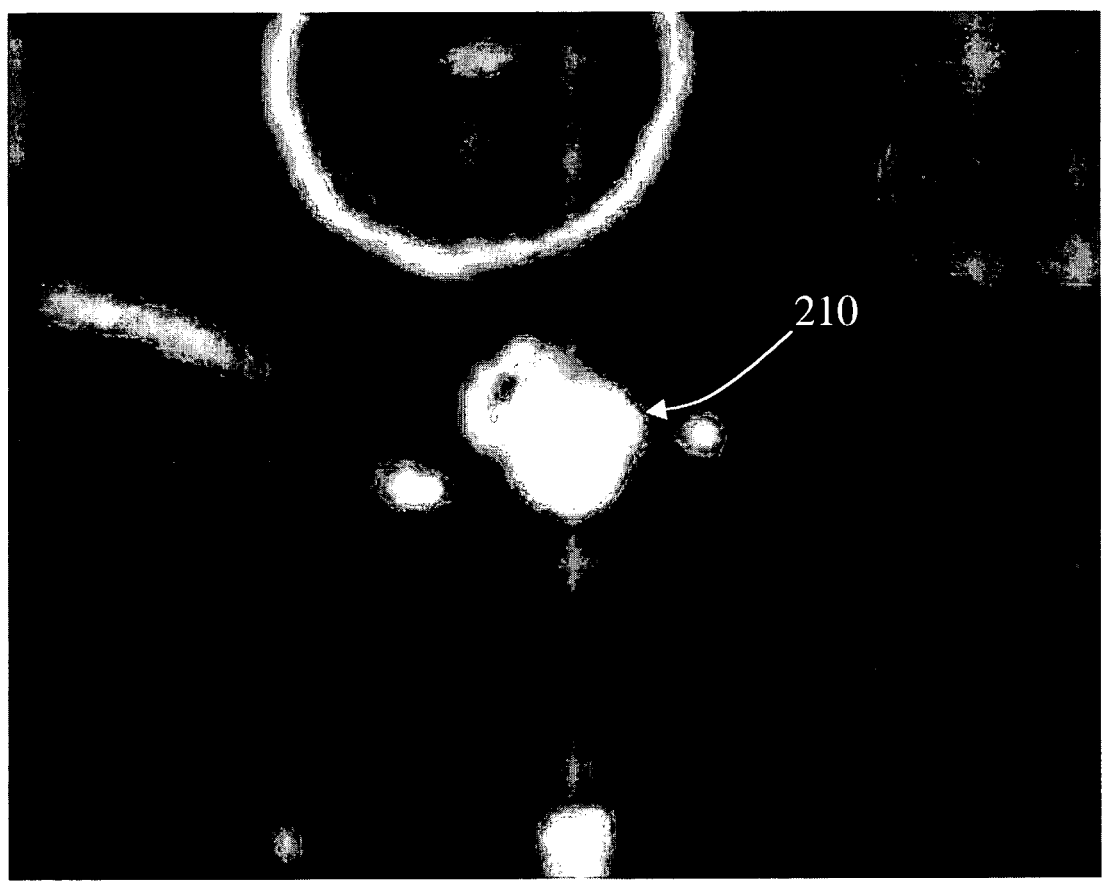
FIG. 2 shows an example of cross sectional view of an aorta according to the present invention.
Figure 3:
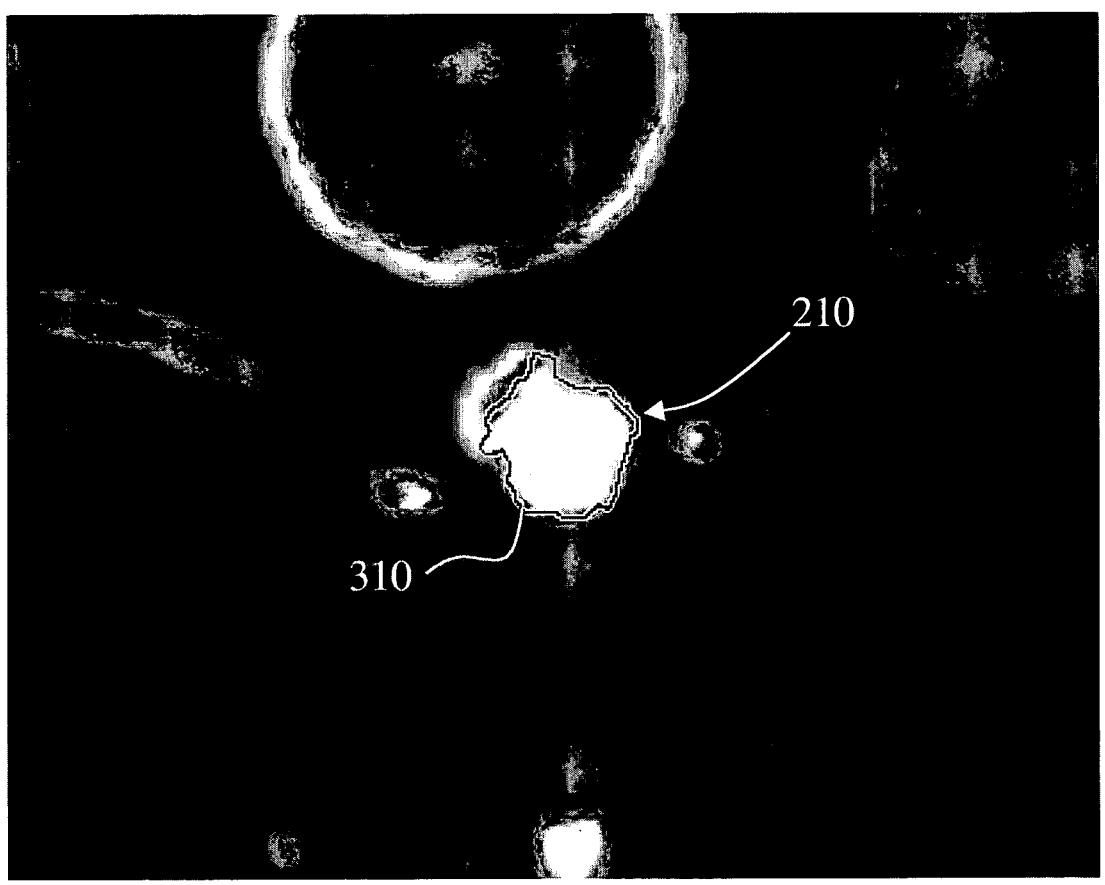
FIG. 3 shows an example of an endoluminal outline according to the present invention.

In one embodiment of the present method a volumetric computed tomography angiography (CTA) dataset is used. To identify the vessel of interest, a user marks two or more points on the CTA. FIG. 1 shows a CTA where three data points are marked on the CTA. One point 110 is marked in the aorta at the inferior real artery (superior to an aneurysm, at the superior extent of the proximal attachment site) and two points 120, 130 at the bifurcation of the common iliac arteries (inferior to the aneurysm, at the distal extent of the distal attachment site). In one aspect of this embodiment, a central path is calculated between these points and perpendicular oblique cross sections of the aorta along its length are extracted. The calculation of the central path is optional, i.e. in case cross sections could be extracted without the centerline calculation, one could omit this step. Cross sections could be obtained at sub-voxel level or at any other level that allows adequate assessment of the radial endoluminal irregularity. FIG. 2 shows an example of a cross section of an aorta 210 for which an irregularity index is determined. The endoluminal outline 310 of this cross section 210 is extracted to only include the flow channel of the vessel. In other words, areas located adjacent to the vessel wall, either inside or outside the vessel wall, which contain calcium or a mural thrombus should not be included in the vessel outline. The endoluminal outline is typically obtained by edge detection and/or adaptive thresholding, techniques which are common techniques in the art. Optionally the obtained endoluminal outline is smoothed with a filter. Since areas with calcium and a thrombus typically appear with a different intensity in the CTA it is possible to distinguish these from the endoluminal outline. Mural calcium typically has an intensity of 300 Hounsfield Units (HU) or more, while the mural thrombus typically has values between −100 and 100 HU. Values for vessel intensity depend on the amount of contrast material injected prior to the study being done, but usually range from 100 to 300 HU. The next step is to determine the cross sectional area of the area outlines by the endoluminal vessel outline, for instance by integration of the pixels enclosed by the outline. This can be done by performing a scan conversion step that identifies the pixels inside the outline.

Figure 4:
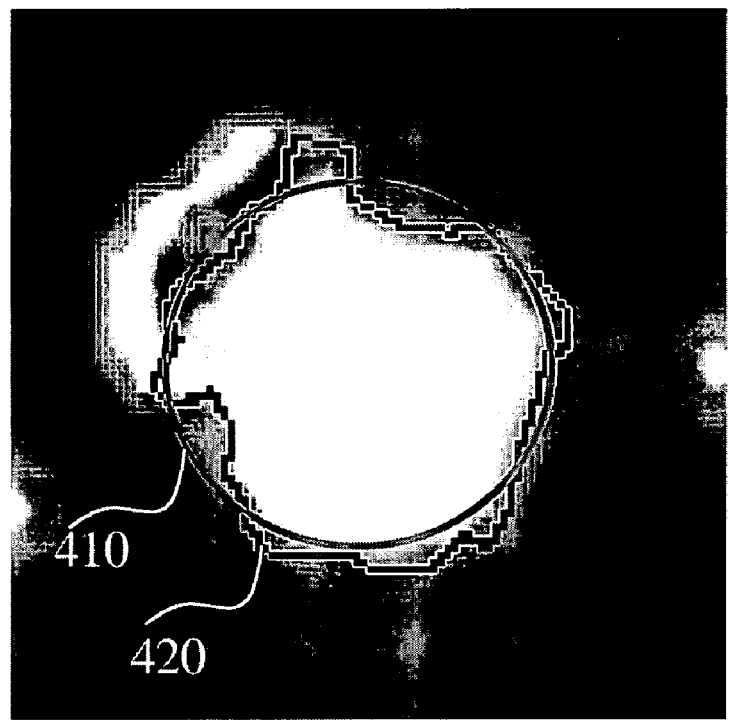
FIG. 4 shows an example of a shape fitted to the endoluminal outline according to the present invention.

Using the determined area of the endoluminal vessel outline, a shape is defined with substantially the same cross sectional area of the one determined for that endoluminal vessel outline. This shape could be preferably a circle, an ellipse or a sphere, however other shapes would also be possible. The selected shape with the same area is now fitted to the endoluminal outline as shown in FIG. 4, for instance, using a least squares method or any optimization method. FIG. 4 shows a circle 410 fitted to outline 420. Note that outline 420 is an enlarged cross section of outline 310.

An irregularity index i is calculated as the ratio of the perimeter of the actual border to the perimeter of the fitted shape with the same cross sectional area as that of the aorta in that image. In general, an irregularity index i could be calculated, not just for the entire perimeter, but also for at least a part (i.e. one or more patches) of the perimeter which then provides an irregularity index for each of those parts (See FIG. 8). The irregularity index is then defined as the ratio of the length of the outline of a selected part of the endoluminal outline to the length of the outline of the fitted shape corresponding to the selected part of the endoluminal outline. The interpretation of the irregularity index is that higher values of i correlate with higher irregularity, since the lowest irregularity for a shape with a given area is attained when that shape is a perfect circle, i.e. 1, in case the selected shape is a circle. It is noted that using this method of an irregularity index standardizes for different cross sectional areas. It is also noted that in one viaration, the distance of the endoluminal outline from the corresponding part of the fitted shape can also be used to calculate, modify or weigh the measured irregularity.

Figure 5:
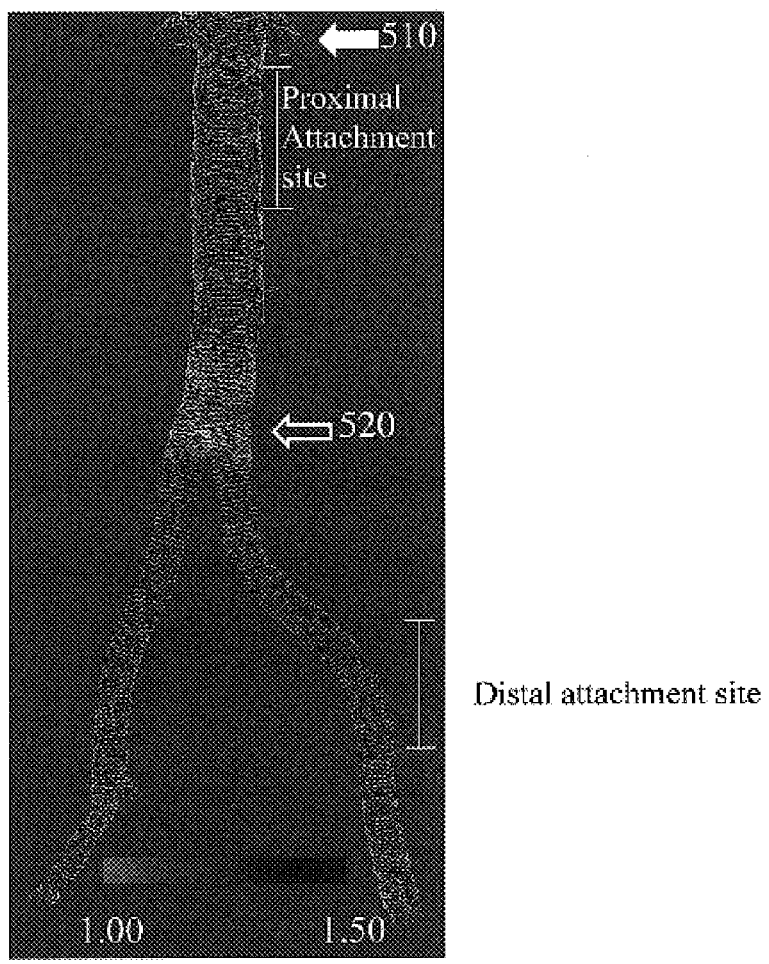
Figure 6:
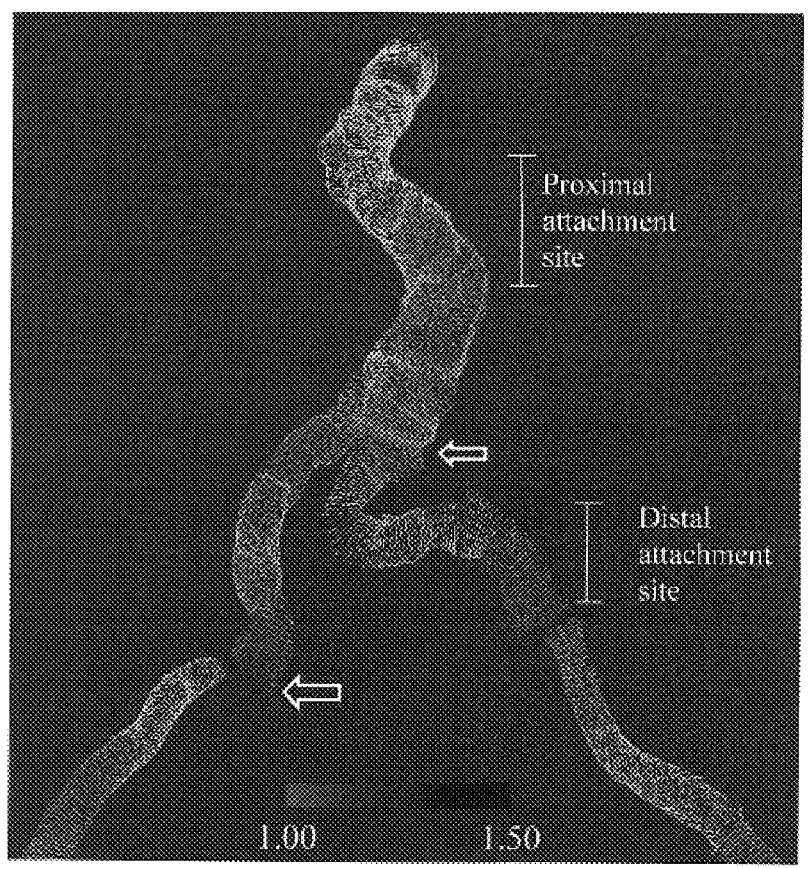
Figure 8:
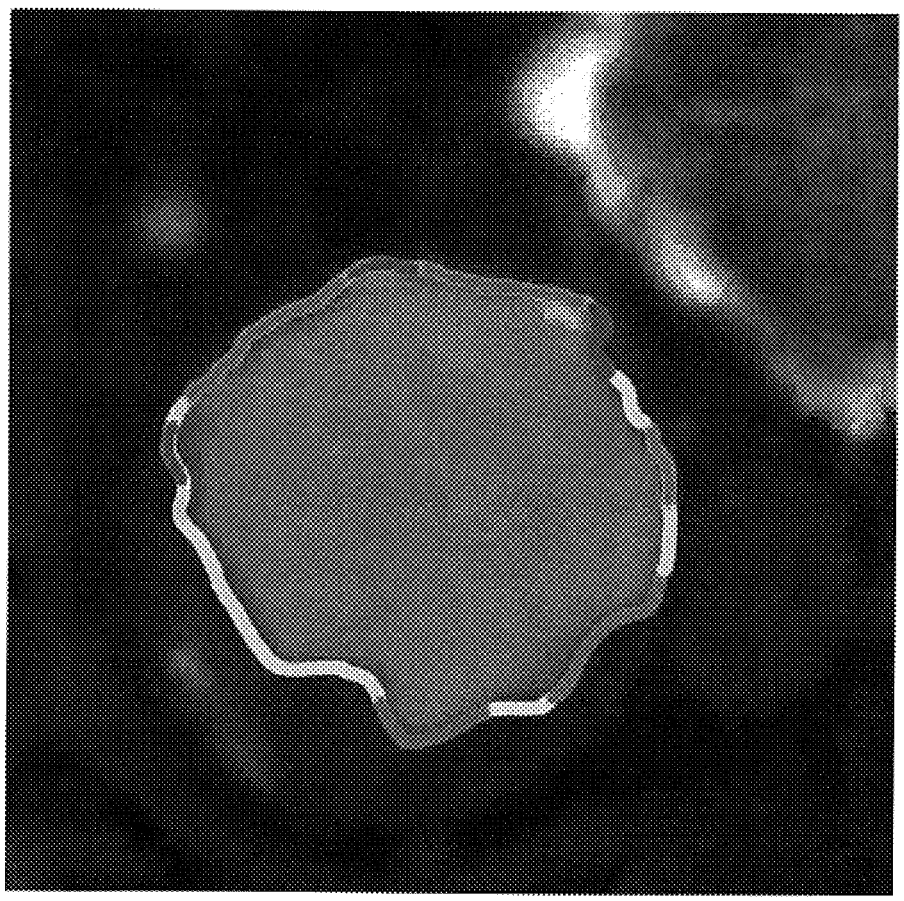
FIG. 8 shows an example of irregularity indices for different part of the endoluminal outline.

The irregularity index could be determined for one cross section but is preferably done for a plurality of cross sections over the length of the selected vessel. In any case, the irregularity index could be visualized or presented using, for instance, but not limited to, a color coding scheme along the vessel, numbers or labels (including fuzzy labels). The visualization of the irregularity index could be done with reference to a range of irregularities encountered in normal patients and in patients with a vascular disease, not limiting to aneurysms. FIGS. 5-8 show different examples of visualization of normal and abnormal vessels with different irregularity indices. FIG. 5 shows a normal aorta with mild irregularity at renal origins (arrow 510) and at the iliac bifurcation (arrow 520). FIG. 6 shows an aneurysmal aorta with irregular proximal and distal stent-graft attachment sites. The distal attachment site had the largest i. The outline arrows show the points where i is artifactually increased at vessel bifurfactions. These areas were not included in the measurements. The irregularity indices in FIGS. 5-6 are shown for each cross section in these images and labeled by a color scheme ranging from green (normal, 1.00) to red (abnormal, 1.50). FIG. 7 shows another way of representing the irregularity index by gray color scheme and numbers for e.g. the proximal neck, distal neck and iliac arteries ranging from normal (ratio of 1) to abnormal levels (ratio larger than 1). FIG. 8 shows an example of different parts (patches) for a vessel outline each with its own irregularity index coded by a color scheme ranging from green (normal), yellow, orange to red (abnormal). These patch irregularities are calculated from the length of the segment and the length of the part of the fitted shape closest to that segment. A weighted average could be employed to calculate the value for a certain patch. Straighter lines will be less irregular than curved lines. The weighting could be accomplished by taking the distance of the endoluminal outline from the corresponding part of the fitted shape.

To validate the present method, we measured irregularity index i in vessel phantoms created using CT simulation/reconstruction software. Phantoms were positioned in the "virtual scanner" at the isocenter and off-isocenter, and scanned longitudinally and transaxially. The image noise in two patient datasets scanned using standard CTA parameters was measured and our simulation software was set to produce, on average, this level of noise in all phantom datasets. The range of vessel sizes and i simulated in phantoms were empirically chosen to include, with a wide margin, the values that would be encountered in the aorta and common iliac arteries. We used three types of phantoms in this validation study. Perfectly regular tapering vessel phantoms with diameters ranging from 2-8 centimeters were used to verify the reliability of measurement in a wide range of vessel sizes. Irregularity was simulated using elliptical vessel phantoms with varying sizes and degrees of eccentricity. Finally, phantoms with continuously varying cross-sectional profiles simulating varying degrees of irregularity were used to approximate the characteristics of vessels in-vivo. Elliptical phantoms had theoretical values of i ranging from 1.00 to 1.60 while phantoms with continuously varying cross-sections simulated a theoretical i of 1.00 to 1.40. Centerlines were obtained through CT reconstructions of these simulated phantoms and measurements of i were compared to the known values using linear regression.

As a result, in regular vessel phantoms, the average measured i was 1.02±0.01, corresponding to a fractional error of measurement of 2±1%. In phantoms simulating irregular vessels, the fractional error in measurement of i was 2±3%, with $R^2$=0.973 ($p<0.001$). The maximal error encountered was an overestimation of i by 11.4%. This occurred in the longitudinal scan of phantoms with the smallest diameter studied (2 centimeters).

To demonstrate the irregularity index measurements in patient datasets, we obtained abdominal aortoiliac CTAs of 5 normal and 15 abnormal patients (13 male, 7 female, mean age 68) with infrarenal AAAs. These patients had their examinations as part of their clinical workup and were chosen consecutively. Measurements of i were made in the anticipated proximal and distal landing zones (aneurysm necks) of an aortoiliac stent-graft (the aorta below renal artery origins to the aneurysm origin and the aorta distal to aneurysm terminus including the entire common iliac arteries respectively) and compared to i measured in the corresponding regions of patients without aneurysms.

As a result, the diameter of the infrarenal aorta and common iliac arteries in patients without aortoiliac disease was 18.9±0.8 mm and 9.7±1.8 mm. The diameter of proximal necks, distal necks and common iliac arteries in abnormal patients was 20.3±2.7 mm, 24.6±2.4 and 15.9±2.7 respectively. In patients without aortoiliac disease, the mean i of proximal and distal infrarenal aorta was 1.05 (95% CI 1.04, 1.06) and 1.06 (95% CI 1.05, 1.06) respectively while in patients with AAAs, the mean i of proximal and distal aneurysm necks was 1.21 (95% CI 1.12, 1.30) and 1.26 (95% CI 1.21, 1.31) respectively. The mean i of normal common iliac arteries was 1.04(95% CI 1.01, 1.06). The mean i was 1.12 (95% CI 1.08, 1.16) in those with AAAs.

The difference between measurements in normal and abnormal patients was statistically significant for each region ($p<0.01$) and overall ($p<0.01$).

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations and other variations are considered to be within the scope and spirit of the present invention as defined by the following claims and their legal equivalents.

What is claimed is:

1. A method for assessing stent-graft attachment sites in a vessel prior to endovascular repair, comprising the steps of:
    (a) determining a radial endoluminal outlines in a cross sectional image of potential stent-graft attachment sites in said vessel;
    (b) determining an area of each one of said endoluminal outlines;
    (c) defining, for each one of said endoluminal outlines, a shape with substantially the same area as said endoluminal outline;
    (d) fitting said shape to said endoluminal outline;
    (e) calculating an irregularity index which is the ratio of at least a part of said endoluminal outline and the outline of said fitted shape corresponding to said at least a part of said endoluminal outline; and
    (f) visualizing said irregularity index with reference to a range of irregularities encountered in normal patients and in patients with a vascular disease.

2. The method as set forth in claim 1, wherein said image is a computed tomography angiograph.

3. The method as set forth in claim 1, wherein said vessel is an infrarenal aorta or a common iliac artery.

4. The method as set forth in claim 1, wherein said vessel is an aneurysmal vessel.

5. The method as set forth in claim 1, wherein said attachment sites are the proximal and distal attachment sites.

6. The method as set forth in claim 1, wherein said step of determining said radial endoluminal outline comprises the step of using edge detection or adaptive thresholding.

7. The method as set forth in claim 1, wherein said step of determining said radial endoluminal outline comprises the step of filtering.

8. The method as set forth in claim 1, wherein said radial endoluminal outline only includes the flow channel of said vessel and excludes calcium or a mural thrombus.

9. The method as set forth in claim 1, wherein said shape is a circle, an ellipse or a sphere.

10. The method as set forth in claim 1, wherein said visualization comprises colors, numbers or labels.

11. The method as set forth in claim 1, further comprising the step of modifying said irregularity index by the distance of said endoluminal outline from said corresponding part of said fitted shape.

* * * * *